United States Patent [19]

Uede et al.

[11] 4,314,914

[45] Feb. 9, 1982

[54] CATALYST SUPPORTING BED

[75] Inventors: Kazuo Uede, Ikoma; Tuguo Sumizaki, Neyagawa; Masatoshi Nakamura, Osaka, all of Japan

[73] Assignee: Koei Chemical Co., Ltd., Osaka, Japan

[21] Appl. No.: 109,024

[22] Filed: Jan. 2, 1980

[30] Foreign Application Priority Data

Mar. 2, 1979 [JP] Japan .................................. 54-24672

[51] Int. Cl.$^3$ ........................ B01J 23/74; B01J 35/02
[52] U.S. Cl. .................................... 252/472; 252/470; 568/472
[58] Field of Search .............. 252/470, 472; 75/134 F; 568/472

[56] References Cited

U.S. PATENT DOCUMENTS 2,780,638  2/1957  Ayers et al. .................... 252/470 X
3,113,972  12/1963  Kodama et al. .................... 568/472
3,565,574  2/1971  Kearby et al. .................. 252/474 X

FOREIGN PATENT DOCUMENTS 1067083  5/1967  United Kingdom ................ 568/473

OTHER PUBLICATIONS

*Easy Way to Formaldehyde*, Chemical Engineering, Nov. 1954, pp. 109–110.

*Primary Examiner*—W. J. Shine
*Attorney, Agent, or Firm*—Lawrence Rosen

[57] ABSTRACT

A catalyst supporting bed in a vertical reactor for production of formaldehyde by gas phase catalytic dehydrogenation of methanol in the presence of a solid metal catalyst, characterized in that the bed is made of a nickel alloy having a nickel content of not less than 25% by weight at least at the surface.

5 Claims, 6 Drawing Figures

CATALYST SUPPORTING BED

The present invention relates to a catalyst supporting bed. More particularly, it relates to a catalyst supporting bed in a vertical reactor for production of formaldehyde according to a gas phase catalytic reaction process.

It is well known to produce formaldehyde by gas phase catalytic dehydrogenation of methanol in the presence of a metal catalyst (e.g. silver, copper). Since the catalytic dehydrogenation requires a relatively high temperature (e.g. 400°–700° C.), the catalyst supporting bed in a vertical reactor where the catalytic reaction substantially proceeds should be made of a material of high heat resistance. As such material, there has been conventionally employed austenite stainless steel. Unfortunately, however, the use of the supporting bed made of this alloy promotes the decomposition of the starting methanol and the produced formaldehyde resulting in by-production of carbon, which is deposited on the supporting bed. Due to such deposition, the micropores or holes in the supporting bed which is usually shaped in a net, a sieve-tray, a grid or the like are clogged and the catalyst layer thereon is raised up so that cracks and gaps are produced in or around the catalyst layer, whereby the conversion of the starting methanol and the yield of the objective formaldehyde are reduced, and ultimately the continuous operation of the reactor becomes impossible. Because of these reasons, the material for the catalyst supporting bed is desired not only to have a high heat resistance but also to cause no decomposition of the starting methanol and the produced formaldehyde.

As the result of an extensive study, it has now been found that the use of a nickel alloy having a nickel content of not less than 25% by weight for construction of the catalyst supporting bed in a vertical reactor for the production of formaldehyde from methanol according to a conventional gas phase catalytic dehydrogenation process is quite effective in overcoming the drawbacks as seen in the use of austenite stainless steel.

Namely, when a catalyst supporting bed of which at least the surface is made of the said nickel alloy is used, no material deposition of carbon in the catalyst bed consisting of the catalyst supporting bed and the catalyst layer thereon is produced. Since the rise of the catalyst layer does not occur, cracks and gaps are hardly produced in and around the catalyst layer. Thus, the catalytic reaction can be continued for a long period of time. Advantageously, the supporting bed made of the nickel alloy is not damaged or bent even after the continuous use at such a high temperature as 400°–700° C. for a long period of time. Besides, the contamination of the catalyst with any decomposition product can be favorably avoided by the use of the said supporting bed.

According to this invention, there is provided a catalyst supporting bed of which at least the surface portion is made of a nickel alloy having a nickel content of not less than 25% by weight, preferably not less than 30% by weight.

The nickel alloy to be used for construction of the supporting bed may comprise, one or more of chromium, molybdenum, iron, copper, titanium, niobium, tantalum, vanadium, etc. Among them, the inclusion of molybdenum in a content of 2.5 to 30% by weight is favorable. Further, the contents of chromium and iron are preferred to be from 1.0 to 30% by weight and not more than 60% by weight, respectively. Specific examples of the preferred nickel alloy are high nickel stainless steel having a nickel content of 25 to 50% by weight, Hastelloy having a nickel content of 45 to 60% by weight, Inconel, etc.

The whole body of the supporting bed may be made of the nickel alloy itself. Alternatively, only the surface portion of the supporting bed may be made of the nickel alloy, for instance, by applying the nickel alloy onto the surface of a shaped body of austenite stainless steel according to a conventional flame spray coating process.

No limitation is present on the shape of the supporting bed, and it may be, for instantce, in the form of a net, a sieve-tray or a grid. Particularly when the supporting bed is made in an incurvated form, a better effect for prevention of cracks or gaps in or around the catalyst layer is obtainable.

Conventional vertical reactors for gas phase catalytic reaction in a fixed bed process have a flat bed. Due to the variation of temperature, the flat bed is subjected to thermal expansion and/or thermal contraction, whereby it is deformed and may cause cracks and gaps to the catalyst layer thereon. Also, the variation of temperature affords directly a serious influence on the catalyst layer. Thus, due to the thermal expansion and/or thermal contraction of the catalyst particles as well as the mutual sintering between the catalyst particles, cracks and gaps may be formed in and around the catalyst layer. Because of these reasons, the continuous operation over a long period of time results in lowering the yield.

Insofar as a flat supporting bed is used, the above tendency is more or less observed in the production of formaldehyde from methanol by gas phase catalytic dehydrogenation, even if it is made of the nickel alloy. Thus, as the result of the continuous operation for a long period of time, cracks and gaps are produced respectively in and around the catalyst layer on the flat bed, and the starting methanol and the oxygen in the air pass through the catalyst layer in an unreacted state. Rather, the oxygen is reacted with the once produced formaldehyde to give formic acid. Due to these reasons, the yield of formaldehyde is lowered.

By the use of an incurvated supporting bed in place of a flat supporting bed, the catalyst layer can be provided thereon in an incurvated state. In the catalyst layer, the compression stress thus works inwardly so that the production of cracks and gaps can be prevented. When desired, a play may be provided around the catalyst layer so as to absorb the expansion of the catalyst layer. Thus, the production of cracks and gaps can be more surely prevented.

BRIEF DESCRIPTION OF THE DRAWING

No limitation is present on the shape of the incurvated section of the bed. Explaining examples of such shape with reference to the accompanying drawing, FIG. 1(a)), an arc of ellipse (cf. FIG. 1(b)), an arc of circle or ellipse with a straight portion at the central part (cf. FIG. 1(c)), an arc of circle with straight portions at the both ends of (cf. FIG. 1 (d)), an arc of ellipse with straight portions at the both ends (cf. FIG. 1(e)), the combination of multiple arcs of circles having different radii of curvature (cf. FIG. 1(f)), etc. Thus, the shape of the incurvated section may be appropriately decided on the diameter of the catalyst layer, the kind of the catalyst, etc. When it is an arc of circle as shown in FIG. 1(a), the ratio of the radius of curvature (R): the diameter of the bed (D) may be usually 1:0.5-2, preferably 1:0.75-1.5. When it is an arc of ellipse as shown in FIG. 1(b), the ratio of the short axis and the long axis may be usually 1:1.5-3.

Figure 1A:
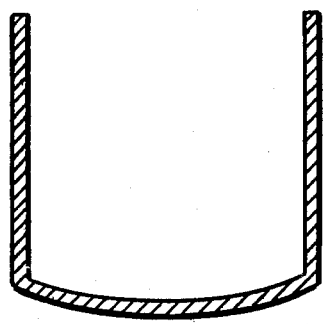
FIG. 1(a) to (f) show respectively the vertical sectional views of several supporting beds. Thus, it may be, for instance, an arc of circle (cf.
Figure 1B:
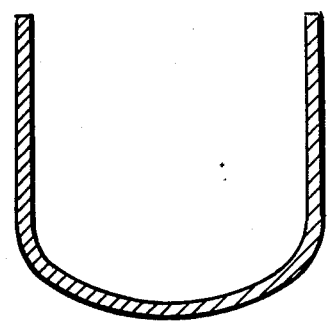
Figure 1C:
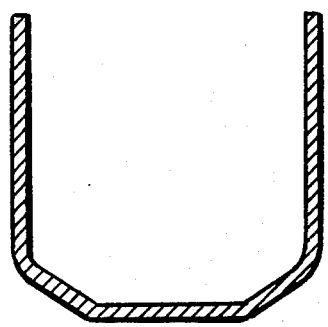
Figure 1D:
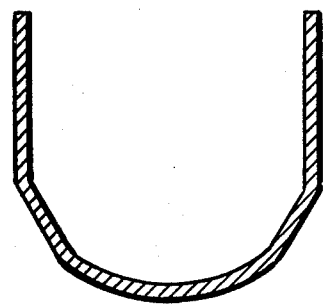
Figure 1E:
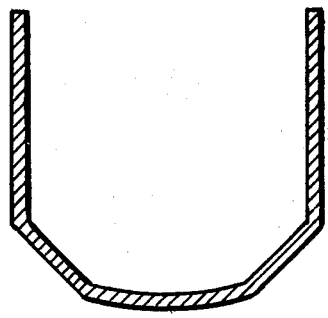
Figure 1F:
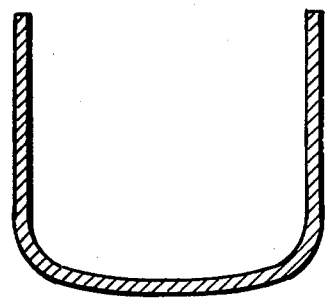

Practical and presently preferred embodiments of this invention are illustratively shown in the following Examples wherein % is by weight.

EXAMPLE 1

In this Example, there was used a vertical reactor of 500 mm in diameter provided with a catalyst supporting bed made of a nickel alloy (Cr, 25%; Ni, 50%; Mo, 6%; Cu, 1%; Ti, 1%; Fe, remainder) and shaped in a sieve-tray having micropores. On the supporting bed, a metal net was placed, and crystalline silver particles of 10 to 40 mesh were put to make a catalyst layer of about 30 mm in thickness. While keeping the temperature of the catalyst layer at a temperature of 640° to 660° C., a mixture of methanol with air was passed through the catalyst layer to produce formaldehyde. The flow rate of the methanol was 150 Nm$^3$/hour, and the molar ratio of the methanol and the air in the mixture was about 1:1.5. After the continuous operation for 150 days, the reaction was interrupted, and the reactor was opened. No material deposition of carbon in the catalyst bed consisting of the supporting bed and the catalyst layer was observed.

EXAMPLE 2

The reaction was carried out in the same manner as in Example 1 but using a catalyst supporting bed made of a nickel alloy (Cr, 15.5%; Ni, 54%; Mo, 16%; W, 4%; Fe, remainder) and shaped in a sieve-tray having micropores. After the continuous operation for 150 days, the reaction was interrupted, and the reactor was opened. No material deposition of carbon in the catalyst bed was observed.

Comparative Example 1

The reaction was carried out in the same manner as in Example 1 but using a catalyst supporting bed made of austenite stainless steel (containing 16 to 18% of Cr, 10 to 14% of Ni and 2 to 3% of Mo) (SUS316) and shaped in a sieve-tray having micropores. From the 13th to 14th day after the initiation of the reaction, the pressure loss was produced; the gaseous pressures in the catalyst layer on the 33th day and the 43th day were respectively 2 times and 3.5 times the gaseous pressure at the initiation of the reaction; on the 43th day, the catalyst layer was raised, and the further operation became impossible. Observation of the catalyst bed revealed the deposition of a considerable amount of carbon therein and the clogging at a portion of the micropores of the supporting bed.

EXAMPLE 3

The reaction was carried out in the same manner as in Example 1 but using a catalyst supporting bed made of a nickel alloy (Cr, 20%; Ni, 25%; Mo, 5%; Fe, remainder), shaped in a sieve-tray having micropores and incurvated in the form of a bowl. After the continuous operation for 150 days, the reaction was interrupted, and the reactor was opened. No material deposition of carbon in the catalyst bed was observed.

EXAMPLE 4

The reaction was carried out in the same manner as in Example 1 but using a catalyst supporting bed made of a nickel alloy (Cr, 20%; Ni, 30%; Mo, 2.5%; Cu, 3%; Fe, remainder), shaped in a sieve-tray having micropores and incurvated in an arc of ellipse at the section. After the continuous operation for 150 days, the reaction was interrupted, and the reactor was opened. No material deposition of carbon in the catalyst bed was observed.

EXAMPLE 5

The reaction was carried out in the same manner as in Example 1 but using a catalyst supporting bed made of a nickel alloy (Cr, 15%; Ni, 72%; Cu, 0.5%; Fe, remainder) and shaped in a sieve-tray having micropores. After the continuous operation for 150 days, the reaction was interrupted, and the reactor was opened. No material deposition of carbon in the catalyst bed was observed.

What is claimed is:

1. A catalyst supporting bed in a vertical reactor for production of formaldehyde by gas phase catalytic dehydrogenation of methanol in the presence of a solid metal catalyst, characterized in that the bed is incurvated and is made of a nickel alloy having a nickel content of not less than 25% by weight at least at the surface.

2. The bed according to claim 1, characterized in that the vertical section of the incurvated bed is in the form of an arc of circle.

3. The bed according to claim 1, characterized in that the vertical section of the incurvated bed is in the form of an arc of ellipse.

4. The bed according to claim 1, characterized in that the vertical section of the incurvated bed is in the form of the combination of arcs of different radii of curvature.

5. The bed according to claim 1, characterized in that the bed is made by applying the nickel alloy onto the surface of body of austenite stainless steel according to a flame spray coating process.

* * * * *